(12) United States Patent
Brown et al.

(10) Patent No.: US 7,368,624 B2
(45) Date of Patent: May 6, 2008

(54) SYNTHESIS FOR POLYCYCLIC AROMATIC HYDROCARBON COMPOUNDS

(75) Inventors: Christopher T. Brown, Rochester, NY (US); Deepak Shukla, Webster, NY (US); Kevin P. Dockery, Rochester, NY (US); Jerome R. Lenhard, Fairport, NY (US); James R. Matz, Fairport, NY (US)

(73) Assignee: Eastman Kodak Company, Rochester, NY (US)

( * ) Notice: Subject to any disclaimer, the term of this patent is extended or adjusted under 35 U.S.C. 154(b) by 687 days.

(21) Appl. No.: 10/812,692

(22) Filed: Mar. 30, 2004

(65) Prior Publication Data

US 2005/0222417 A1    Oct. 6, 2005

(51) Int. Cl.
  C07C 2/00   (2006.01)
  C07C 2/02   (2006.01)
(52) U.S. Cl. ........................... 585/422; 585/426
(58) Field of Classification Search ................ 585/425
  See application file for complete search history.

(56) References Cited

U.S. PATENT DOCUMENTS

| 2,238,180 | A | 4/1941 | Moergeli et al. |
| 4,505,858 | A | 3/1985 | Mayer |

FOREIGN PATENT DOCUMENTS

| JP | 98330295 | 12/1998 |
| JP | 2002-110353 | 4/2002 |
| JP | 2003-104916 | 4/2003 |

OTHER PUBLICATIONS

Sartori et al. J Org. Chem. 1993, 58, 7271-7273.*
Braun, J, Manz, G., Julius v. Brun und Gottfired Manz: Fluoranthen und seine Derivate (VI. Mitell.), 1937, pp. 1603-1610.
Lang, K. F., et al, 1.16-Benzperiflanthen, Chem., Ber., 1962, pp. 673-675.
Kovacic, P., et al, "Polymerization of Benzene to p-Polyphenyl by Ferric Chloride", 1963, pp. 1864-1868.
Sep, W. J. et al, "Formation of Aromatic Radical-Cations by Oxidation with Electronegatively Substituted Quinones in Acid Media; Kinetics and Mechanism", 1979, vol. 35, pp. 2161-2168.
McKillop, A., et al, J. Am. Chem. Soc., "Thallium in Organic Synthesis. 58. Regiospecific Intermolecular Oxidative Dehydrodimerization of Aromatic Compounds to Biaryls Using Thallium(III) Trifluoroacetate", 1980, 102, pp. 6504-6512.
Kovacic, P. et al, "Dehydro Coupling of Aromatic Nuclei by Catalyst-Oxidant Systems: Poly (p-phenylene)", Chem Rev., 1987, 87, pp. 357-379.
Mitchell, R. H., et al, "Straining Strained Molecules. III. The Spectral and Mutagenic Properties and an Alternate Synthesis of Diaceperylene and Dicyclopental[1,2,3-cd: 1',2', 3'-Im]perylene", Can. J. Chem. 70, 1992, pp. 1015-1021.

Anton, U., et al, "Synthesis of n-Alkyl-Substituted Perylenes and Terrylenes via Alkali-Metl Induced Cyclization of Oligonaphthylenes", Chem. Ber., 1992, 125, pp. 2325-2330.
Percec, V. et al, "Synthesis of Aromatic Polyethers by Cation-Radical Polymerization", Makromol. Chem., Macromol. Symp. (1992), 54/55, pp. 337-356.
Wassmundt, F. W., et al, "Soluble Catalysts for Improved Pschorr Cyclizations", J. Org. Chem. 1995, 60, pp. 196-201.
Ciminale, F. et al, "Aminium Salts-Induced Dimerization of a-Methylstyrene and 1-Aryl-1-Phenylehylenes. Solvent Effect.", Tetrahedron, vol. 52, No. 44 (1996), pp. 13971-13980.
Debad, J. D., et al, "Dibenzotetraphenylperiflanthene: Synthesis, Photophysical Properties, and Electrogenerated Chemiluminescence", J. Am. Chem. Soc. 118, (1996), pp. 2374-2379.
Debad, J. D., et al, "Anodic Coupling of Diphenylbenzo[k]fluoranthene: Mechanistic and Kinetic Studies Utilizing Cyclic Voltammetry and Electrogenerated Chemiluminescence", J. Org. Chem., 62, (1997), pp. 530-537.
Wirth, T., et al, "Hypervalent IodineCompounds: Recent Advances in Synhetic Applications", Synthesis, No. 8, (1999), pp. 1271-1287.
Dotz, F., et al, "Synthesis of Large Polycyclic Aromatic Hydrocarbons: Variation of Size and Periphery", J. Am. Chem. Soc., 122, (2000), pp. 7707-7717.
Tsuda, A., et al, "Fully Conjugated Porphyrin Tapes with Electronic Absorption Bands that Reach into Infrared", vol. 293, (2001), pp. 79-82.
Gryko, D. T., et al, "A Simple and Versatile One-Pot Synthesis of meso-Substituted trans-$A_2B$-Corroles", J. org. Chem., 66, (2001), pp. 4267-4275.
Wehmeier, M., et al, "Novel Perylene Chromophores Obtained by a Facile Oxidative Cyclodehydrogenation Route", Chem. Eur. J., 7, No. 10, pp. 2197-2205.
Ciminale, F., et al "Acid Catalysis in the Aminium Hexachloroantimonate-Induced Cyclodimerization of 1-Aryl-1-phenylethylenes", Eur. J. Org. Chem., (2002), pp. 3850-3854.
Fabrizio, E. F., et al, "Photophysical, Electrochemical,and Electrogenerated Chemiluminescent Properties of 9,10-Dimethyl-7,12-diphenylbenzo[k]fluoranthene and 9,10-Dimethylsulfone-7,12-diphenylbenzo[k]fluoranthene", J. Phys. Chem., 106, (2002), pp. 1961-1968.
Cristiano, M. L. S., et al, "Investigations into the Mechanism of Action of Nitrobenzene as a Mild Dehydrogenating Agent Under Acid-Catalysed Conditions", Org. Biomol. Chem., 1, (2003), pp. 565-574.
Gryko, D. T., et al, "Simple Route to Meso-Substituted Trans-$A_2B_2$-Porphyrins Bearing Pyridyl Units", Tetrahedron Letters, 44, (2003) pp. 3317-3321.

* cited by examiner

Primary Examiner—Yvonne Eyler
Assistant Examiner—Yevgeny Valenrod
(74) Attorney, Agent, or Firm—Arthur E. Kluegal

(57) ABSTRACT

A process for forming an aryl-aryl bond comprises the step of reacting an arene hydrocarbon compound with either (1) an organic oxidant selected from the group consisting of a quinone, a quinone imine, a quinone diimine, and a nitroarene, or (2) an oxidizing salt selected from the group consisting of a triarylaminium salt, an oxonium salt, and a nitrosium salt, or (3) a hypervalent iodine compound, each in the presence of a Brönsted or Lewis acid.

32 Claims, No Drawings

SYNTHESIS FOR POLYCYCLIC AROMATIC HYDROCARBON COMPOUNDS

FIELD OF THE INVENTION

This invention relates to the field of organic syntheses and to a process for forming an aryl-aryl bond either intramolecularly or intermolecularly or both. This process is exemplified in the preparation of bis-fluoranthenes or indeno and diindeno[1,2,3-cd:1',2',3'-lm]perylenes. The term indenoperylene refers to a perylene core with an indene fusion between the 1,2,3 and/or 1',2',3' positions of indene and cd and/or lm faces of perylene. [See The Naming and Indexing of Chemical Substances for Chemical Abstracts-A Reprint of Index IV (Chemical Substance Index Names) from the Chemical Abstracts—1992 Index Guide; American Chemical Society: Columbus, Ohio, 1992; paragraph 135,148 and 150. Debad, J. D.; Morris, J. C.; Lynch, V.; Magnus, P.; Bard, A., *J. Am. Chem. Soc.* 1996, 118, 2374-2379]. In this specification, the term indenoperylene is also used to more generally describe materials wherein the fusion between indene's 1,2,3 positions and perylene's cd faces is not limited solely to indene as defined by the above reference. In this case indene can also include analogous materials wherein the benzo-group of indene can be a ring of 5, 6, or 7 atoms comprising carbon or heteroatoms such as nitrogen, sulfur or oxygen.

In addition this method is exceptionally useful in the intramolecular formation of either a five or six (as described for indenoperylenes) membered ring. Five membered rings found in materials such as fluoranthenes can also be prepared using this method.

BACKGROUND OF THE INVENTION

Large polycyclic aromatic hydrocarbons have become useful materials and have necessitated synthetic methods to prepare them. Additionally, dimers of polycyclic aromatic hydrocarbons have become useful materials and have necessitated improved methods for preparing them. Finally, indenoperylenes and diindenoperylenes have become useful materials and have necessitated synthetic methods for preparing them. In the following publications synthetic details have been provided for preparing indenoperylenes: (a) Schlichting, P.; Rohr, U.; Müllen, K. *Liebigs Ann./Reculeil* 1997, 395-407. (b) Feiler, L.; Langhals, H.; Polborn, K. *Liebigs Ann.* 1995, 1229-1244. (c) Debad, J. D.; Morris, J. C.; Lynch, V.; Magnus, P.; Bard, A. *J. Am. Chem. Soc.* 1996, 118, 2374-2379. (d) Anotn, U.; Göltner, C.; Müllen, K. *Chem. Ber.* 1992, 125, 2325-2330. (e) Wehmeier, M.; Wagner, M.; Müllen, K. *Chem. Eur. J.,* 2001, 2197-2205 (f) Bard, A. J.; Magnus, P.; Morris, J. C.; Debad, J. D. *J. Org. Chem.* 1997, 62, 530-537. Further disclosures describing their utility in OLED applications are found in Patents and applications EP 1,148,109 A2; EP 1,182,244 A1; EP 1,235, 466 A2, U.S. Pat. No. 6,004,685, 82452US, 84436US, 84435US, JP 2001-338764-A, JP 2003-104916-A, JP 2002-110353-A; JP 2002-110355-A; JP 2002-110356-A; JP 1998-30295-A; JP 2002-025772-A; JP 2000-86549-A; JP 2002-025773-A; JP 2000-48958-A.

Manz et al report preparations of periflanthene using sodium amide to dimerize and oxidatively cyclodehydrogenate from fluoranthene to give periflanthene.

Bard et al described the preparation of dibenzo{[f,f']-4, 4',7,7'-tetraphenyl}-diindeno[1,2,3-cd:1',2',3'-lm]perylene (A) from 7,12-diphenylbenzo[k]fluoranthene. The critical oxidizing reagent used to achieve the oxidative cyclodehydrogenation to form A was cobalt(III)fluoride. Additionally, Bard, et. al. have demonstrated that the cyclizations can be performed on a small scale using electrochemical techniques.

Müellen et al have used iron(III)chloride to prepare similar indenoperylenes. Mitsui Chemical also reports a similar approach.

Quinones have been reported as organic oxidants with diphenyl disulfides, but only polymeric materials have been isolated (E. Tsuchida, K. Yamamoto, M. Jikei, H. Hiroyuki, *Macromolecules,* 1990, 930-934). Triarylaminium oxidants have been used (F. Ciminale, L. Lopez, G. Farinola, S. Sportelli, A. Nacci, *Eur. J. Org. Chem.,* 2002, 3850-3854; F. Ciminale, L. Lopez, V. Paradiso, A. Nacci, *Tetrahedron,* 1996, 13971-13980), but not to form aryl-aryl bonds. Hypervalent iodine compounds have been used to form aryl-aryl bonds (T. Kitamura, Y. Fujiwara, *Organic Preparations and Procedures International,* 1997, 409-458; A. Varvoglis, *Tetrahedron,* 1997, 1179-1255), but these processes have been limited to activated arenas.

Most recently TDK has reported the use of a Yamamoto (nickel) coupling strategy to bring on the dimerization of a fluoranthene and subsequent cyclization to an indenoperylene.

Because of the utility of these materials, there is a need to provide a process for preparing these materials in higher yields and with improved purity.

SUMMARY OF THE INVENTION

The invention provides a process for forming an aryl-aryl bond comprises the step of reacting an arene hydrocarbon compound with either (1) an organic oxidant selected from the group consisting of a quinone, a quinone imine, a quinone diimine, and a nitroarene, or (2) an oxidizing salt selected from the group consisting of a triarylaminium salt, an oxonium salt, and a nitrosium salt, or (3) a hypervalent iodine compound, each in the presence of a Brönsted or Lewis acid.

The invention enables preparing the desired materials in higher yields and with improved purity.

DETAILED DESCRIPTION OF THE INVENTION

As described, in one embodiment the process of the invention comprises the step of reacting an arene hydrocarbon compound with an organic oxidant, selected from the group consisting of a quinone, a quinone imine, a quinone diimine, and a nitroarene, in the presence of a Brönsted or Lewis acid and wherein the reaction is preferentially terminated with a quenching agent. Another embodiment provides a process for forming an aryl-aryl bond comprising the step of reacting an arene hydrocarbon compound with an oxidizing salt, selected from the group consisting of a triarylaminium salt, an oxonium salt, and a nitrosium salt, in the presence of a Brönsted or Lewis acid. A further embodiment provides a process for forming an aryl-aryl bond comprising the step of reacting an unactivated arene hydrocarbon compound with a hypervalent iodine compound in the presence of a Brönsted or Lewis acid. The invention process may also be used in the formation of oligomers and polymers of arenes. The invention provides a process to prepare these materials in higher yields and improved purity.

The invention process is summarized above and comprises a method for forming one or more aryl-aryl carbon bonds. Such a bond may be intermolecular or intramolecular, and more than one bond of either type may be formed in a single process. The process further comprises the step of reacting an arene hydrocarbon compound with an organic oxidant or an oxidizing salt in the presence of a Brönsted and/or Lewis acid and terminating the reaction by an electron transfer step effected by the addition of a suitable quenching donor. The organic oxidants are selected from the group consisting of a quinone, a quinone imine, a quinone diimine, and a nitroarene. The oxidizing salts are selected from the group consisting of a triarylaminium salt, an oxonium salt, and a nitrosium salt. The process further comprises the step of reacting an unactivated arene hydrocarbon compound with a hypervalent iodine compound in the presence of a Brönsted or Lewis acid.

In selecting the organic oxidant, the Brönsted and Lewis acids, and the quenching donor, materials are preferably chosen so as to not otherwise interfere with process as well as have suitable solubility and stability in the reaction solvent.

Arene hydrocarbons are a class of materials well known in the chemical literature and include single as well as linked or fused aromatic rings which may be further substituted. A particular class of arene hydrocarbons for which this invention process is particularly useful includes polycyclic aromatic hydrocarbons. Polycyclic aromatic hydrocarbons are molecules made up of three or more rings at least two of which are aromatic and in which at least two of these aromatic rings are fused by sharing two adjacent carbon atoms. Illustrative examples of arene hydrocarbons that could be used in the present invention are shown in Table 1.

TABLE 1

Examples of Arene Hydrocarbon Substrates.

1 

2 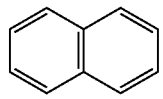

3 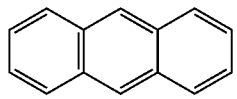

4 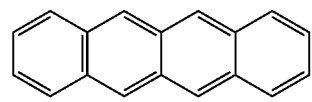

5 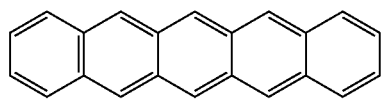

6 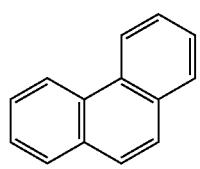

TABLE 1-continued

Examples of Arene Hydrocarbon Substrates.

7 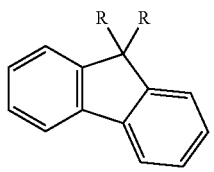

8 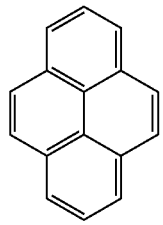

9 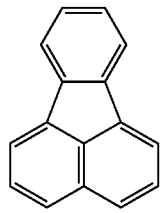

10 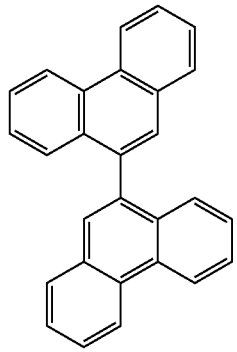

11 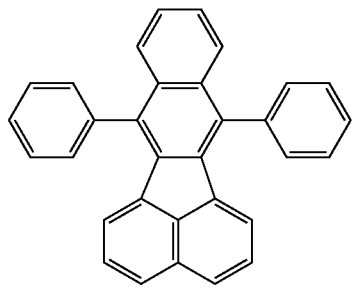

12 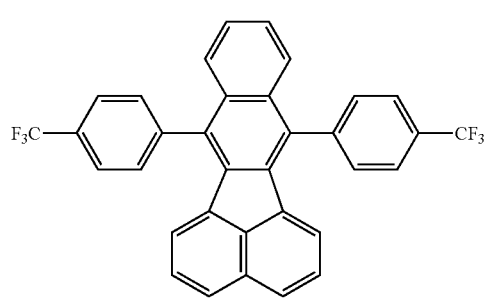

TABLE 1-continued

Examples of Arene Hydrocarbon Substrates.

13
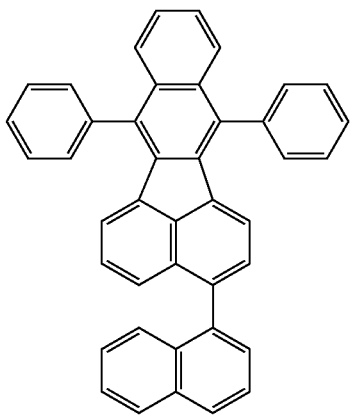

14
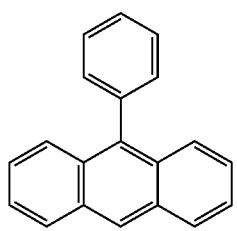

15
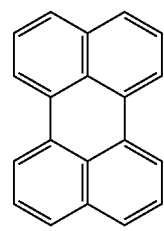

16
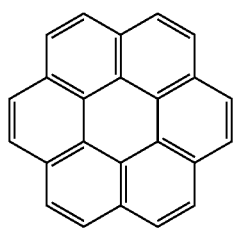

17
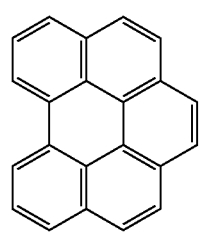

18
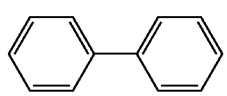

TABLE 1-continued

Examples of Arene Hydrocarbon Substrates.

19
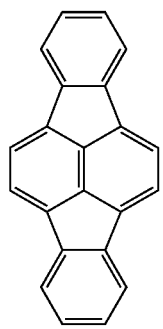

20
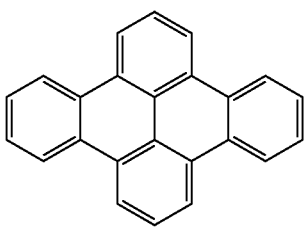

21
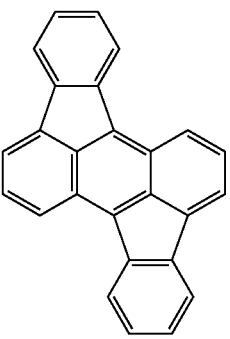

22
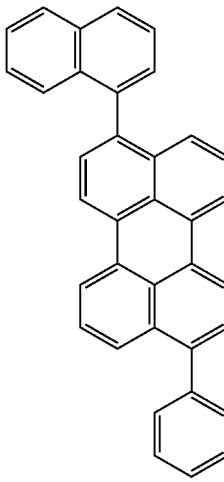

Suitable organic oxidants for the invention process can be selected from a wide variety of such materials known to those skilled in the synthetic arts. These oxidants include substituted and unsubstituted quinones and quinone derivatives such as quinone imines and quinone diimines, hypervalent iodine compounds, nitroarenes, triarylaminium salts, oxonium salts, and nitrosium salts.

Particularly useful examples of such oxidants include substituted and unsubstituted quinones, substituted and unsubstituted quinone imines, and substituted and unsubstituted quinone diimines, described by the formulas I and II where X may be individually chosen to be O or NR and where $R^1$, $R^2$, $R^3$, $R^4$, $R^5$ are independently selected as hydrogen or substituents such as alkyl, alkenyl, alkynyl, alkylhalo, cycloalkyl, cycloalkenyl, alkylthio, alkoxy, halo, carboxylic acid, carboxylate ester, nitro, sulfonic acid, sulfonate ester, sulfonic acid amide and cyano. The groups may also be incorporated into a ring system, for example to form polyaromatic quinones or polyaromatic quinone diimines such as 1,4-naphthoquinone. This list of substituents is meant to be illustrative rather than limiting.

In one useful embodiment of the invention process, the quinone oxidant is 2,3-dichloro-5,6-dicyanobenzoquinone. Illustrative examples of quinone oxidants that could be used in the present invention are shown in Table 2.

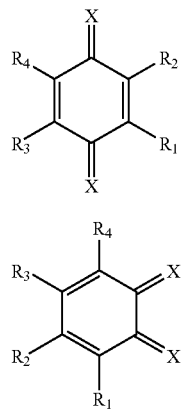

TABLE 2

Examples of Quinone Oxidants.

| 23 | 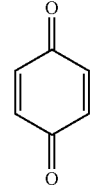 |
|---|---|
| 24 | 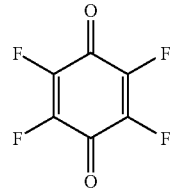 |
| 25 | 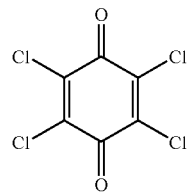 |
| 26 | 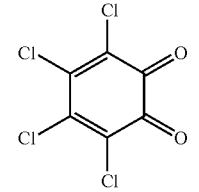 |
| 27 | 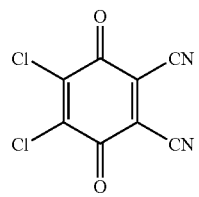 |
| 28 | 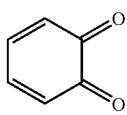 |
| 29 | 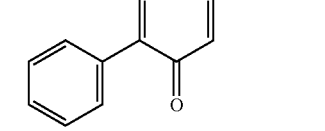 |
| 30 | 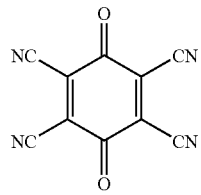 |
| 31 | 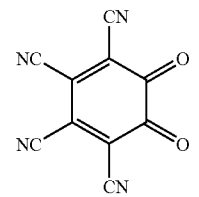 |

TABLE 2-continued

Examples of Quinone Oxidants.

32 [structure: 2,5-dichloro-3,6-di-tert-butyl-1,4-benzoquinone]

33 [structure: N,N'-dimethyl-1,4-benzoquinone diimine]

34 [structure: 1-methyl-1H-benzotriazole-4,7-dione]

An additional class of oxidants useful in the present invention is nitroarenes (formula III),

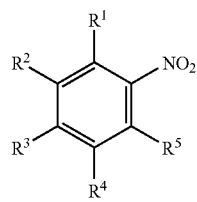

III where $R^1$, $R^2$, $R^3$, $R^4$, $R^5$ are independently selected as hydrogen or substituents such as alkyl, alkenyl, alkynyl, alkylhalo, cycloalkyl, cycloalkenyl, alkylthio, alkoxy, halo, carboxylic acid, carboxylate ester, nitro, sulfonic acid, sulfonate ester, sulfonic acid amide. The groups may also be incorporated into a ring system, for example to form polyaromatic nitroarenes such as nitronaphthalenes. This list of substituents is meant to be illustrative rather than limiting. Examples of some nitroarenes useful to the invention are provided in Table 3.

TABLE 3

Examples of Nitroarene Oxidants

35 [structure: 1,3-dinitrobenzene]

TABLE 3-continued

Examples of Nitroarene Oxidants

36 [structure: nitrobenzene]

37 [structure: 1,2-dinitrobenzene]

38 [structure: 1,3,5-trinitrobenzene]

39 [structure: 3,5-dinitrobenzenesulfonic acid]

40 [structure: 3,5-dinitro-2-nitrobenzoic acid derivative]

A class of oxidizing salts useful to the present invention is triarylaminium salts as shown in formula IV, $Ar_3N^+ \cdot X^-$

IV $Ar =$ 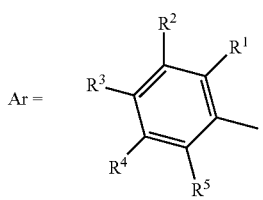

where each Ar can be independently selected where $R^1$ to $R^5$ are independently selected as hydrogen or substituents such as alkyl, alkenyl, alkynyl, alkylhalo, cycloalkyl, cycloalkenyl, halo, carboxylic acid, carboxylate ester, nitro, sulfonic acid, sulfonate ester, sulfonic acid amide, with the proviso that at least one group of $R^1$ to $R^5$ be a covalent bond to an aminium nitrogen. The triarylaminium in formula IV may be added as a salt or generated in situ. Examples of counterions $X^-$ include tetrafluoroborate, hexafluoroantimonate, hexafluorophosphate, and hexachloroantimonate. Examples of some triarylaminium salts useful to the invention are shown in Table 4 where in each case a counterion X is implied.

TABLE 4

Examples of Triarylaminium Oxidants

41 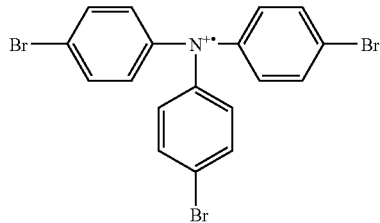

42 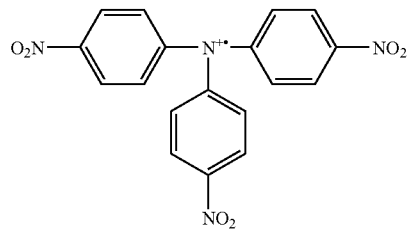

43 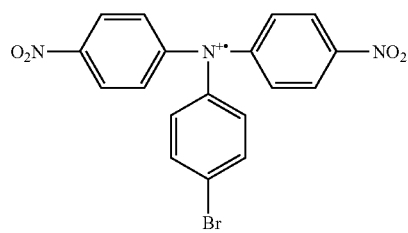

44 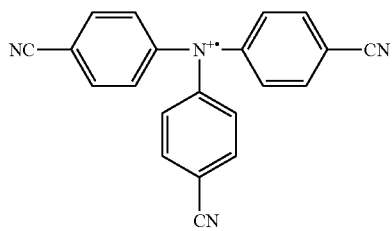

45 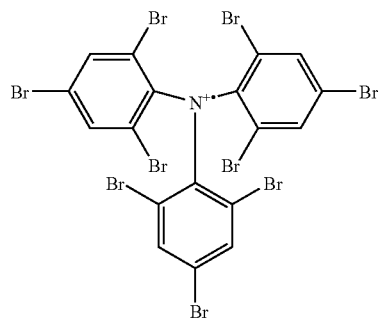

46 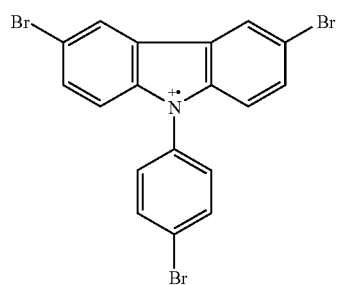

TABLE 4-continued

Examples of Triarylaminium Oxidants

47 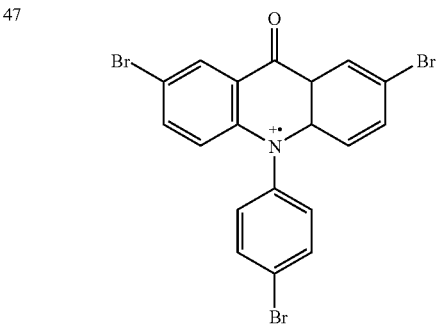

An additional class of oxiding salts useful to the invention is oxonium salts. Examples of oxonium salts are provided in Table 5.

TABLE 5

Examples of Oxonium Salts

48 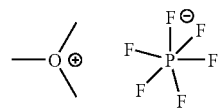

49 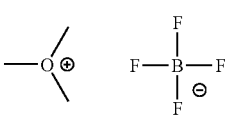

50 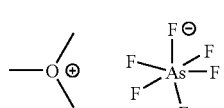

51 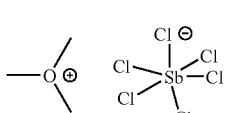

A further class of oxidizing salts useful to the invention is nitrosonium salts. Examples of nitrosonium salts are provided in Table 6.

TABLE 6

Examples of Nitrosonium Salts.

52 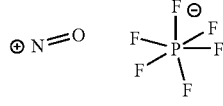

53 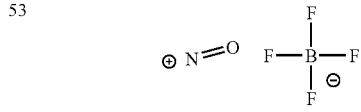

TABLE 6-continued

Examples of Nitrosonium Salts.

54 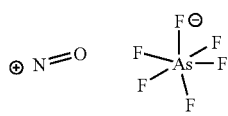

55 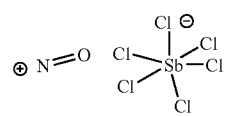

TABLE 7

Examples of Hypervalent Iodine Oxidants

56 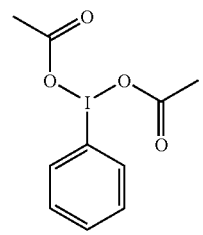

57 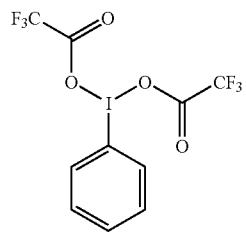

58 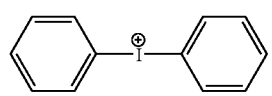

59 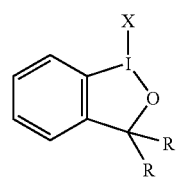

60 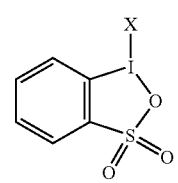

61 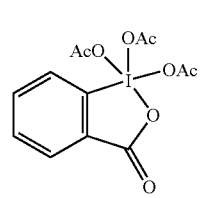

An additional class of organic oxidants that may be used in the present invention includes hypervalent iodine oxidants. These materials have been described in the literature for the formation of aryl-aryl bonds, but only in cases where the arene hydrocarbons have been activated towards oxidation by substitution with one or more alkyloxy groups. This severely limits the application of the process to a constrained set of synthetic targets. This invention provides a process which can be used to form intermolecular and intramolecular aryl-aryl bonds from arene hydrocarbons that do not have alkyloxy activation.

The class of hypervalent iodine compounds is comprised of organic iodine-containing oxidants in which iodine assumes the +3 or +5 oxidation state (formulas V and VI, where X may be individually chosen to be carboxylate, sulfonate, or a further substituted oxygen) and where $R^1$, $R^2$, $R^3$, $R^4$, $R^5$ are independently selected as hydrogen or substituents such as alkyl, alkenyl, alkynyl, alkylhalo, cycloalkyl, cycloalkenyl, alkylthio, alkoxy, halo, carboxylic acid, carboxylate ester, nitro, sulfonic acid, sulfonate ester, sulfonic acid amide. The groups $R^1$ and X may also form a ring system. This list of substituents is meant to be illustrative rather than limiting. Illustrative examples of such materials are shown in Table 7. In one useful embodiment of the invention process, the hypervalent iodine oxidant is phenyliodine(III)bis(trifluoroacetate).

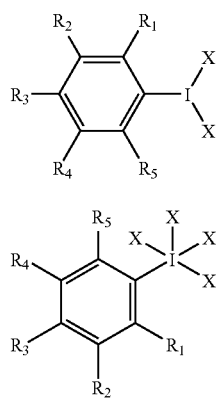

Both Brönsted and Lewis acids are classes of materials well described in the chemical literature. Brönsted acids are generally defined as proton donors while Lewis acids are more broadly defined as compounds containing a vacant orbital which can accept an unshared pair of electrons from a base (see, for example, R. P. Bell, The Proton in Chemistry, second edition, Cornell University Press, Ithaca, N.Y. 1973). Examples of Brönsted acids are presented in Table 8. In preferred embodiments of the invention, the Brönsted acid is chosen from among trichloroacetic acid, trifluoroacetic acid, trifluoromethanesulfonic acid, methanesulfonic acid, fluorosulfonic acid, and hexafluoroisopropanol. The Brönsted acids may also be used in combination, such as a combination of trifluoroacetic acid and methanesulfonic acid.

TABLE 8

Examples of Brönsted Acids

| | |
|---|---|
| 62 | $CF_3SO_3H$ |
| 63 | $C_6H_5SO_3H$ |
| 64 | $CH_3SO_3H$ |
| 65 | $CF_3CO_2H$ |
| 66 | $CCl_3CO_2H$ |
| 67 | $CHCl_2CO_2H$ |
| 68 | $CFH_2CO_2H$ |
| 69 | $CClCH_2CO_2H$ |
| 70 | $HCO_2H$ |
| 71 | $C_6H_5CO_2H$ |
| 72 | $CH_3CO_2H$ |
| 73 | $HBF_4$ |
| 74 | $H_2SO_4$ |
| 75 | $FSO_3H$ |
| 76 | $HPF_6$ |

In the present invention, Lewis acids are used for generating an oxidant capable of generating the requisite hydrocarbon radical cations. In the scope of the invention, a Lewis acid is defined as any species that is capable of accepting an electron-pair (IUPAC Compendium of Chemical Terminology, The Gold Book, Second Edition, A. D. McNaught and A. Wilkinson, Blackwell Science, 1997). In the scope of the present invention Lewis acids include chemical species that are proton sources (Brönsted and Arrhenius acids).

Suitable Lewis acid for the process according to the present invention are based on metals from Groups, IIA, IIB, IIIA, IIIB, IVB, IVA, VA, VB, VIB and VIIB of the Periodic Table of the Elements.

The Group IIB Lewis Acids have the general formula (VII):

$$MX_2 \quad\quad\quad (VII)$$

wherein M is a Group IIB metal; X is a halogen or an organic ligand.

The Group IIIA and IIIB Lewis Acids can also be represented by the formula (VIII):

$$R_n MX_{(3-n)} \quad\quad\quad (VIII)$$

wherein n is equal to 1 or 2, each R is either the same or different aryl or alkyl C1 to C15 linear or cyclic group, and each X is the same or different halogen; and wherein M is a Group IIIA or IIIB metal.

The Group IVB and IVA Lewis acids have the general formula (IX):

$$MX_4 \quad\quad\quad (IX)$$

wherein M is a Group IVB metal and X is a ligand, preferably a halogen. Nonlimiting examples include titanium tetrachloride, zirconium tetrachloride, or tin tetrachloride.

The Group VB and VA Lewis Acids have the general formula (X)

$$MX_y \quad\quad\quad (X)$$

wherein M is a Group V metal, X is a ligand, preferably a halogen, and y is an integer from 3 to 5. Nonlimiting examples include vanadium tetrachloride and antimony pentafluoride.

In one embodiment of the present invention Lewis acids that are useful in the present invention contain an element from rows I-V of the Periodic Table. Lewis acid comprising an element from rows I-IV of the Periodic Table is preferred in the present invention. Lewis acids containing an element from rows I-III of the Periodic Table are especially preferred.

In another embodiment of the present invention, Lewis acids containing an element from group IIA-VIIb or IIB-VA of the Periodic Table are particularly useful. The Lewis acids comprising an element from group IIA-IIIB or IIIA-IVA of the Periodic Table are preferred in the present invention. Lewis acids comprising an element from group IVB or IIIAA of the Periodic Table are especially preferred in the present invention.

According to another embodiment of the invention Lewis acids that contain a compound of B, Al, Ti, Zr, Sn, Sb, Sc, La, or Zn are particularly useful in the present invention. In another aspect of the present invention, Lewis acids containing a halogen or an organic ligand are useful. Lewis acids containing a halogen are preferred. Lewis acids containing a fluoro or chloro group are particularly preferred. In another embodiment, Lewis acids containing an organic ligand selected from $CF_3SO_3^-$, $CH_3CO_2^-$, and $NO_3^-$ are particularly useful in the present invention.

Illustrative examples of Lewis acids preferred in the present invention are shown by the formulae in Table 9, but the invention is not limited to thereto.

TABLE 9

Examples of Lewis Acids

| | |
|---|---|
| 77 | $BF_3$ |
| 78 | $BF_3 \cdot (C_2H_5)_2O$ |
| 79 | $BCl_3$ |
| 80 | $AlCl_3$ |
| 81 | $Al(CH_3)_3$ |
| 82 | $TiCl_4$ |
| 83 | $ZrCl_4$ |
| 85 | $SnCl_4$ |
| 86 | $SnCl_4 \cdot 5H_2O$ |
| 86 | $SnF_4$ |
| 87 | $VCl_4$ |
| 88 | $SbF_5$ |
| 89 | $ScCl_3$ |
| 90 | $ScCl_3 \cdot 6H_2O$ |
| 91 | $Sc(CF_3SO_3)_3$ |
| 92 | $La(CH_3CO_2) \cdot XH_2O$ |
| 93 | $LaCl_3$ |
| 94 | $LaCl_3 \cdot 7H_2O$ |
| 95 | $LaF_3$ |
| 96 | $La(NO_3)_3 \cdot 6H_2O$ |
| 97 | $La(C_2O_4)_3 \cdot xH_2O$ |
| 98 | $La(SO_4)_3 \cdot xH_2O$ |
| 99 | $La(CF_3SO_3)_3$ |
| 100 | $ZnCl_2$ |
| 101 | $ZnBr_2$ |
| 102 | $ZnF_2$ |
| 103 | $Zn(CH_3CO_2)_2$ |
| 104 | $Zn(CH_3CO_2)_2 \cdot 2H_2O$ |
| 105 | $ZnSiF_6 \cdot xH_2O$ |
| 106 | $Zn(NO_3)_2 \cdot xH_2O$ |
| 107 | $Zn(C_2O_4)_2 \cdot xH_2O$ |
| 108 | $Nd(CF_3SO_3)_3$ |

A particularly useful Lewis acid in the present invention is boron trifluoride, usually utilized as its diethylether complex.

Advantageously, Brönsted and Lewis acids can be combined together in the present invention. One desirable embodiment of the present invention uses trifluoroacetic acid with boron trifluoride diethyletherate.

In the invention process, it is preferable to use a quenching agent to terminate the reaction, which can improve the purity and yield of the desired product. The invention process is believed to proceed by a mechanism that involves cationic intermediates such as cation radicals, and suitable quenching agents are materials that can affect an electron transfer to convert the radical cationic intermediates into a non-reactive species. Such quenchers are widely known in the literature (Oxidizing and Reducing Agents; Handbook of Reagents for Organic Synthesis, S. D. Burke and R. L. Danheiser, Wiley, 1999) and include, but are not limited to, inorganic reducing agents such as Li, Na, K, Zn, Mg, Co, Fe, Al, Sn and their complexes such as $FeCl_2$ and $SnCl_2$; organic reducing agents such as aliphatic and aromatic amines, alcohols, aromatic ethers; and heterocycles containing nitrogen and/or sulfur; organometallic reducing agents such as the metal cyanides hexacyanoferrate and hexacyanoruthenate, and metallocenes such as ferrocene and zirconocene. Preferred quenching agents are those that are commercially available and inexpensive, soluble in the reaction medium, electrochemically active yet chemically unreactive towards the cation radical intermediate, and in addition, are readily separable from the reaction product mixture.

In the invention process; metals are not preferred because they introduce additional risks (e.g, fire) and purification challenges. Zinc has been demonstrated to perform very well as a reductive quench agent for substrates such as those disclosed in the present invention, however, when stoichiometric quantities of metals are used to affect the quench step a large quantity of ionic and elemental metal remain and must be separated from reaction products. Such a step can be difficult for typical products and often requires Soxhlet extractions or mineral acid digestions to effect product isolation of pure product.

Among the organic and organometallic quenching agents, the propensity for a given quenching agent to effect the reduction of the cationic reaction intermediate is dependent on the ability of the quenching agent to release an electron. A measure of this ability to release an electron is given by the electrochemical oxidation potential of the quenching agent. In general, the most potent quenching agents are those with the lowest (least positive) electrochemical oxidation potential. Such electrochemical oxidation potentials are reported in the literature, see for example, Electrochemical Reactions in Nonaqueous Systems C. Mann and K. Barnes, (Editors) Marcel Dekker, New York (1970) and Encyclopedia of Electrochemistry of the Elements, Organic Section, Volumes XI-XV, A. Bard and H. Lund (Editors) Marcel Dekker Inc., New York (1984), permitting the selection of suitable quenching agents. Examples of quenching agents useful in the present invention are shown in Table 10.

Among the various quenching agents that may be used in this invention, the more preferred are those from the aromatic amine, aromatic ether, and organometallic class of quenchers. The most preferred quenching agent is ferrocene.

TABLE 10

| Examples of Quenching Agents | |
|---|---|
| 109 | Zn |
| 110 | Mg |
| 111 | Fe |
| 112 | Co |
| 113 | Ferrocene |
| 114 | Zirconocene |
| 115 | Li |
| 116 | Na |
| 117 | K |
| 118 | Al |
| 119 | Sn |
| 120 | Methanol |

TABLE 10-continued

| Examples of Quenching Agents | |
|---|---|
| 121 | (triethylamine structure) |
| 122 | (triphenylamine structure) |
| 123 | (trimethoxybenzene structure) |
| 124 | (1,3,5-trimethoxybenzene structure) |
| 125 | (1,4-dimethoxybenzene structure) |

The invention process is particularly useful for dimerizing members of a class of materials generally described as polycyclic aromatic hydrocarbons and comprises the step of an intermolecular oxidative dimerization and/or oxidative cyclization to form a desired material. An example of the utilization of this process is shown in the conversion of the general Formula (XI) to form the bis-fluoranthene, Formula (XII), or perylene core of the indenoperylene and diindenoperylenes, Formula (XIII) and Formula (XIV) respectively. Two specific examples of the utility for this new method will be described. First, the three step preparation of dibenzo{[f,f']-4,4',7,7'-tetraphenyl}-diindeno[1,2,3-cd:1',2', 3'-lm]perylene is described Second, a five step process for preparing benzo{[f]-4,7-diphenyl}-indeno[1,2,3-cd] perylene is described. Both of these methods are advantaged to any described previously because of a shorter synthetic sequence and higher purity. The purity is typically improved for this process due to the minimization of undesirable halogenated impurities typically seen with iron(III)chloride or unreacted haloaromatics employed in metal mediated coupling chemistry (Negishi, E. -I., Handbook of Organopalladium Chemistry for Organic Synthesis; Editor, de Meijer, A.; John Wiley and Sons, 2003).

The acenaphthylene compound is represented by Formula (XI):

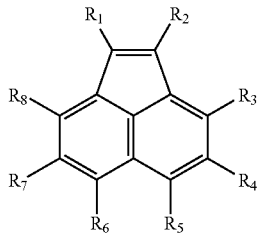

(XI)

wherein $R_1$, $R_2$, $R_3$, $R_4$, $R_5$, $R_6$, $R_7$ and $R_8$ are independently selected as hydrogen or substituents;

The bis-fluoranthene compound is represented by Formula (XII):

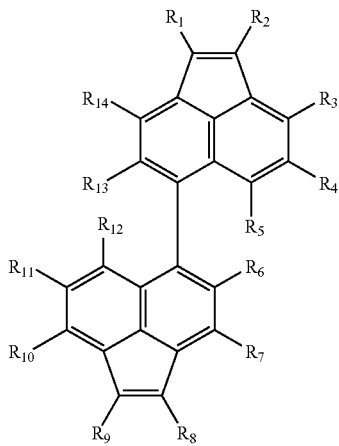

(XII)

wherein $R_1$-$R_{14}$ are independently selected as hydrogen or substituents.

The diindenoperylene compound is represented by Formula (XIII):

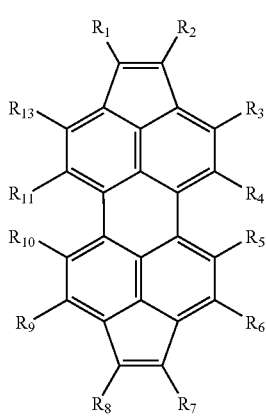

(XIII)

wherein $R_1$-$R_{13}$ are independently selected as hydrogen or substituents;

The indenoperylene compound is represented by Formula (XIV)

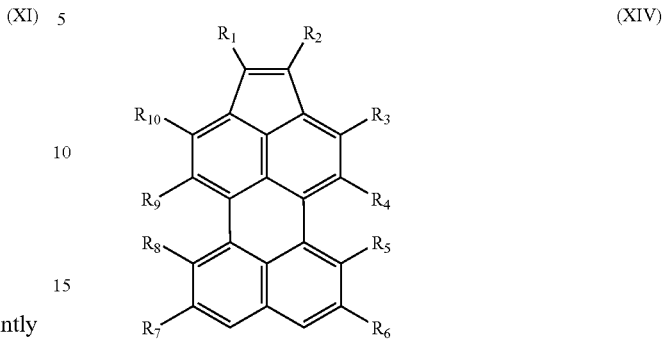

(XIV)

wherein $R_1$-$R_{14}$ are independently selected as hydrogen or substituents.

Embodiments of this invention may be advantaged relative to existing art in that the process is simple and does not require prior activation of the aromatic hydrocarbon, e.g. Suzuki, Negishi, Yamamoto and Miyaura, Stille Couplings. (Negishi, E. -I. Handbook of Organopalladium Chemistry for Organic Synthesis; Editor, de Meijer, A.; John Wiley and Sons, 2003). Further, embodiments of this invention may provide a process for shorter reactions and higher overall yields than many processes described in the art. Embodiments of the invention may be chosen so as to avoid expensive and potentially toxic cobalt (II) salts and the need for potentially troublesome electrochemical equipment. Finally, the embodiments of the invention provide exceptional purity and typically without the necessity for chromatography. Unlike many of the processes described in the art, embodiments of this method may also minimize metal and halogen contamination in the final products, which is particularly desirable if the final products are to be used in the construction of electronic devices such as an organic light emitting diode (OLED) electroluminescent (EL) device.

Unless otherwise specifically stated, use of the term "group", "substituted" or "substituent" means any group or radical other than hydrogen. Additionally, when reference is made in this application to a compound or group that contains a substitutable hydrogen, it is also intended to encompass not only the unsubstituted form, but also its form further substituted with any substituent group or groups as herein mentioned, so long as the substituent does not destroy properties necessary for the intended utility. Suitably, a substituent group may be halogen or may be bonded to the remainder of the molecule by an atom of carbon, silicon, oxygen, nitrogen, phosphorus, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentylphenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecylphenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy) acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

EXAMPLES

Synthesis of dibenzo{[f,f']-4,4'7,7'-tetraphenyl}-diindeno[1,2,3-cd:1',2',3'-lm]perylene The scheme of the overall preparation of dibenzo{[f,f']-4,4',7,7'-tetraphenyl}-diindeno[1,2,3-cd:1',2',3'-lm]perylene is exemplified in Scheme 1. This invention is directed toward the step where XV (7,12-diphenylbenzo[k]fluoranthene) is converted to XVI and XVII.

Synthesis of A

A 3 L round bottom flask was charged with 1,3-diphenylacetone (200 g, 0.95 mol), acenaphthenequinone (173.3 g, 0.95 mol) and 1.4 L of ethanol and heated to near reflux. A solution of potassium hydroxide (29.3 g, 0.52 mol) in 285 ml of ethanol was added slowly to a mechanically stirred solution under nitrogen. After complete addition the reaction (black suspension) was stirred an additional thirty minutes at reflux and then cooled to 15° C. and filtered. The solids collected were washed with another 1 L of ethanol. The solids were resuspended in 1 L of methanol and filtered. Finally, the black solids collected were washed with 1 L of methanol until the filtrate was clear to yield 307.76 g of product (91% yield).

Scheme 1

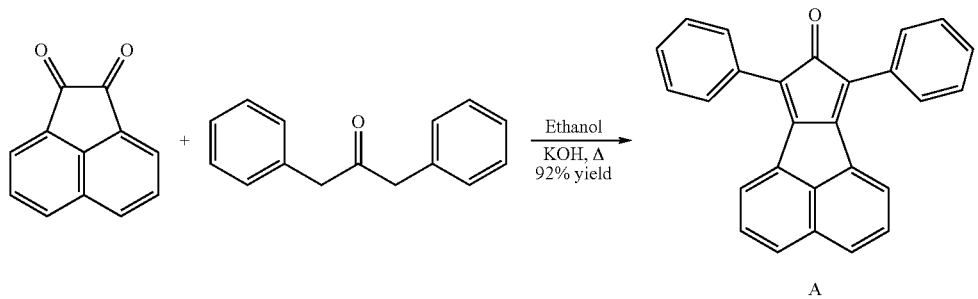

A

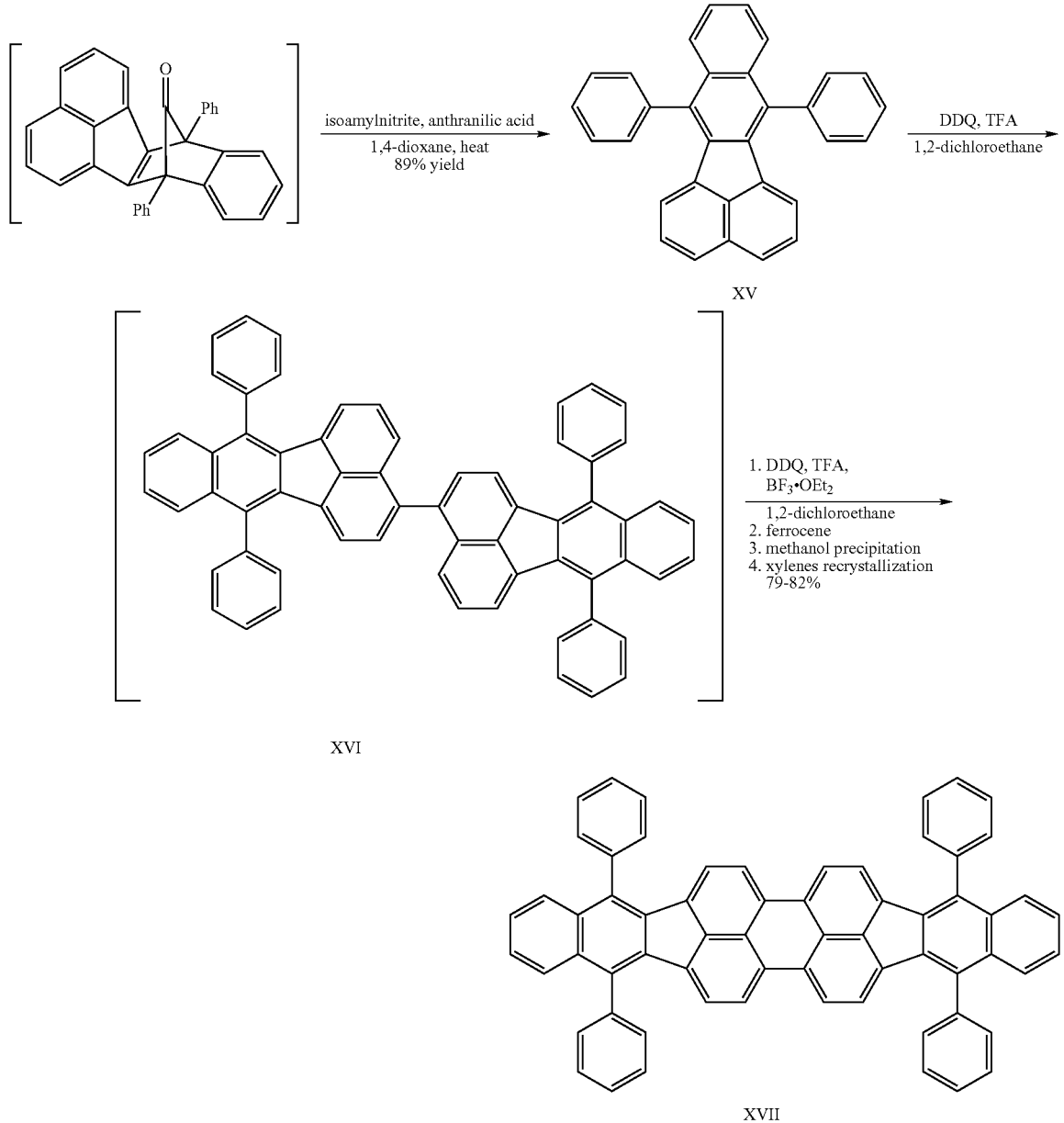

Synthesis of XV

A 3 L round bottom flask with a mechanical stirrer and reflux condenser was charged with acecyclone (100 g, 0.281 mol) and 1.2 L of 1,2-dichloroethane. The reaction vessel was affixed with two addition funnels. The first contained a solution of anthranilic acid (40.40 g, 0.295 mol) in 500 ml of 1,2-dichloroethane. The second contained isoamyl nitrite (134.8 ml, 1.003 mol) in 365 ml of 1,2-dichloroethane. After bringing the reaction mixture to reflux the solutions in the two addition funnels were added dropwise and simultaneously in equal volumes to the reaction over a period of approximately 1.4 hours. The reflux condenser must be affixed in such a manner as to return solvent directly back into the reaction mixture and not into either addition funnel solution. It is critical that the addition step be performed with great caution as the reaction is highly exothermic and effervescent. If the addition is conducted to quickly a foaming eruption will occur. It is also critical the reaction temperature be at reflux prior to initiation otherwise a buildup of diazotized anthranilic acid may occur and upon thermal initiation overwhelm the reaction vessel and thermal sink. Shortly after complete addition the bubbling ceased and the reaction color changed from black to dark yellow, indicating consumption of acecyclone. The reaction was refluxed an additional hour, and the reaction mixture solvents were stripped by simple distillation until a thick yellow paste formed. These solids were triturated with 2 L of hot butanol, collected and then triturated from hot methanol and collected, washed with 1 L of methanol and dried to provide 105.42 grams of yellow solid for a 92% yield. Thin layer chromatography, 20% dichloromethane/heptane, $R_f$=0.8, clean blue spot.

Invention, Synthesis of XVII, Version A

A 5 L round bottom flask was fixed with a mechanical stirrer and a nitrogen inlet. The flask was charged with XV (41.52 g, 0.103 mol), 1,2-dichloroethane (600 ml) and trifluoroacetic acid (176 ml). This mixture was stirred at 0-5° C. and one equivalent of 2,3-dichloro-5,6-dicyanobenzoquinone (DDQ) was added as a solid in portions over a period of one hour. Following the addition the reaction was monitored by TLC (50% $CH_2Cl_2$/heptane, XV $R_f$=0.7; XVI $R_f$=0.5; reaction aliquots quenched with ferrocene in dichloromethane prior to TLC) and once all XV was converted to XVI then 40 ml of $BF_3$—$OEt_2$ was added all at once. Subsequently another equivalent of DDQ was added as a solid in portions over a period of 1 hour. The progress of the reaction was monitored by TLC, and once all of XVI was converted to XVII the ferrocene (38.5 g, 0.206 mol) was added and the reaction stirred for 2 hours to assure complete quench of radical cations and reduction of remaining DDQ. The crude XVII was precipitated with methanol (2.8 L) and stirred for 2 hours. The purple solids were collected and washed with 500 ml of methanol. LC-assay of this crude material indicated 98 area percent purity. These solids were suspended in 1 L of triethylamine and stirred vigorously under a nitrogen atmosphere and then heated to 35° C. and stirred for 1 hour and allowed to cool to room temperature. The product is precipitated with the addition of 1 L of methanol. The solids were collected by filtration through a glass wool filter pad. These solids were then suspended in 2 L of 10% $HCl_{(aq)}$ and stirred vigorously under a nitrogen atmosphere and then heated to 35° C. and stirred for 1 hour at which time the solids were collected by filtration. These solids were then suspended in 2 L of water and stirred vigorously for 1 hour at 35° C. under a nitrogen atmosphere and the solids were subsequently collected and triturated in 2 L of hot methanol with vigorous mechanical stirring. Solids were collected and dried overnight. The solids were triturated under a nitrogen blanket in 2.5 L of xylenes overnight. The reaction was cooled to room temperature and allowed to stand overnight. The solids were collected, dried and then triturated a second time in 2.5 L of xylenes as performed previously. A Soxhlet extraction can also be utilized at this stage with improved purification results but the thimble must have a mechanical stirrer to keep the solids from packing down in the thimble and avoid extremely slow extraction. Alternatively, the solids were triturated with vigorous stirring for 1 hour at 35° C. in 1 L of acetonitrile under a nitrogen atmosphere. The reaction was cooled to room temperature and the solids were collected and dried under high vacuum (yield: 32.86 g (79%)). Assay by LC was 99.3 area percent. The solids were then baked at 350° C. for 12 hours under high vacuum with stirring to remove residual solvents. TGA indicate 0.12% volatiles remaining. NMR: $\delta_H$ (500.05 MHZ, $C_2D_2Cl_4$) 7.76 (8H(7)), 7.84 (8H(9)), 7.83 (4H(10)), 7.82 (4H(11)), 7.47 (4H(12)), 6.74 (4H(14)), 8 (4H(15)), 13C NMR (500.05 MHZ, $C_2D_2Cl_4$) 139.1(1), 137.1(2), 136.8(3), 135.6 (4), 134.9(5), 133.4(6), 130.5(7), 130.4(8), 129.5(9), 128.3(10), 127.3(11), 126.2(12), 126 (13), 123.5(14), 122.1(15)

Structure 1 Numbering Legend for XVII NMR Data

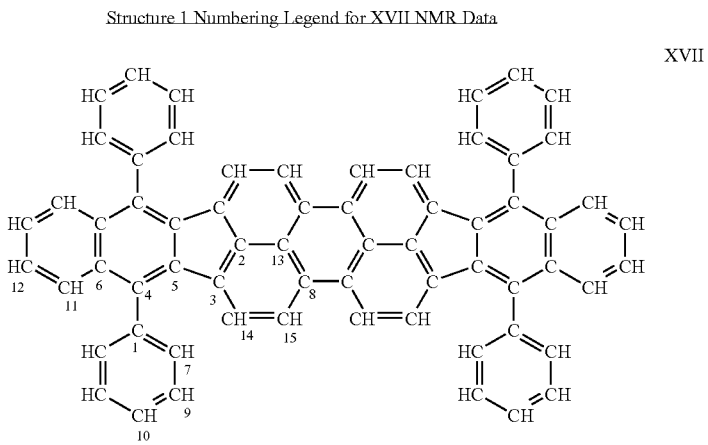

Structure 1 Numbering Legend for XVII NMR Data

Invention, Synthesis of XVII, Version B

Add 5.19 g (12.8 mmol) of XV, 32 mL of trifluoroacetic acid, and 100 mL of dichloroethane to a 500 mL reactor. Sweep the vessel with nitrogen and cool the solution to −5° C. Add 2.76 g (12.2 mmol, 0.95 eq.) of 2,3-dichloro-5,6-dicyano-1,4-benzoquinone in 11 equal portions over 1 h. The time between the 11 additions is every 6 minutes and the quantity of each addition is 0.25 g. After the oxidant has been completely added, stir for 1 h at −5° C. Add 3.0 mL of, boron trifluoride etherate, all at once and then add an additional 2.76 g (12.2 mmol, 0.95 eq.) of 2,3-dichloro-5,6-dicyano-1,4-benzoquinone in 11 equal portions over 1 h. After this addition is complete, stir the reaction mixture for 2 h at −5° C. Add 4.76 g (25.6 mmol) of solid ferrocene all at once and stir for 1 h while warming to 20° C. A slight exotherm (1-2° C.) is observed. Slowly add 300 mL of methanol to the mixture to precipitate the product and stir for 2 h. Collect the solids by filtration, washing twice with 50 mL of methanol. Reflux the air-dried product with 75 mL of triethylamine for 1 h, cool 50° C. and add 300 mL of methanol to help precipitate the product. Collect the solid and wash twice with 50 mL of methanol. The assay of the crude product at 254 nm should be about 99.2 area percent. Slurry the damp solid with 200 mL of methanol and 50 mL of 5% $HCl_{(aq)}$ at 70° C. for 1 h and collect the product after cooling to 40° C. Re-slurry the damp solid with 250 mL of methanol at 70° C. for 1 h and collect the product after cooling to ambient temperature and dry the product at 60° C. for 3 h. Place the product in a Soxhlet thimble and extract with 310 mL of toluene until no color remains in the extract phase. Cool the product solution to ambient temperature and stir for 2 h. Collect the product filtration and wash with a solution of 50 mL of a 1:1 heptanes/toluene solution. Then wash the filter cake twice with 50 mL of heptanes. The product is then dried for 48 h under vacuum at 100° C. to give 4.7-4.8 g (90-95% yield) of XVII as a reddish/copper colored solid. Assays are 99.5-99.7 area percent.

Invention Synthesis of XVII from XVI via the Use of Nitrobenzene and Trifluoromethanesulfonic Acid, Version C A suspension of XVI (0.42 mmol/mL) in a solution of 10 v/v % trifluoromethanesulfonic acid in nitrobenzene was stirred at room temperature for 4 h. The reaction was then quenched with a solution of 3 v/v % triethylamine in 1,2-dichloroethane to afford XVII in 91% yield (based on absorbance measurements of the quenched reaction mixture). Product was never isolated.

Comparative, Synthesis of XVII

As reported by Debad, J. D.; Morris, J. C.; Lynch, V.; Magnus, P.; Bard, A., *J. Am. Chem. Soc.* 1996, 118, 2374-2379, XVII can be prepared by reacting XV with excess cobalt(III)fluoride at reflux in trifluoroacetic acid to provide crude XVII with an LC-assay of 66 area percent and a subsequent 56% yield following chromatography. This yield and purity is considerably less than that achieved with the invention process.

Comparative, Synthesis of XVII

In a manner similar to that reported by Wehmeier, M.; Wagner, M.; Müllen, K. *Chem. Eur. J.,* 2001, 2197-2205 iron (III) chloride may also be used to effect the dimerization and cyclization required to convert XV to XVII. A typical reaction is: A 500 ml round bottom flask is charged with XV and 267 ml of dichloromethane. The resulting mixture is bubbled with nitrogen for 15 minutes (the bubbling is continued throughout the course of the reaction) prior to the addition of subsequent reagents. A solution of 12.7 grams of iron(III) chloride in 20 ml of nitromethane (previously degassed with nitrogen) was added dropwise over a five minute period to the solution of XV. After complete addition of the Iron solution the reaction was stirred an additional 10 minutes being sure to maintain vigorous nitrogen sparging. At this stage 500 ml of degassed methanol is added an the reaction is allowed to stir over night to precipitate the product. Solids are collected and washed with methanol. After drying a "crude" yield of 2.22 g (83%) is obtained with an LC assay of 81.4 area percent. This material requires extensive purification (e.g., chromatography, extractions) to remove halogenated product and residual iron (the impurities are typically on the order of several percent by weight each) from the reaction. These multiple purification steps make this process impractical for large scale manufacturing and can significantly reduce product yield below that achieved in the invention process. As noted above, these impurities can make the product less suitable for use in the fabrication of electronic devices.

Conclusions for Advantages of the Inventive Method for the Synthesis of XVII

The inventive methods versions A and B clearly demonstrate the advantages of purity and yield over commonly used existing synthetic methods disclosed by Muellen or Bard et al. The yields of XVII using the inventive reaction are typically greater than 90%, see version A and C. Early methods wherein multiple recrystallizations were performed still yielded 79% of product. All samples of XVII prepared also provided purity levels typically greater than 99 area percent. It is clear from these three inventive examples that the inventive reaction is far superior to the comparative examples wherein yields of crude material range from 56-83% with high levels of metal and/or halogen contamination (i.e., 66 and 81 area percent assay by HPLC).

Synthesis of benzo{[f]-4,7-diphenyl}-indeno[1,2,3-cd]perylene

The scheme of the overall preparation of benzo{[f]-4,7-diphenyl}-indeno[1,2,3-cd]perylene is exemplified in Scheme 2. This invention is directed toward the step where XIX is converted to XX.

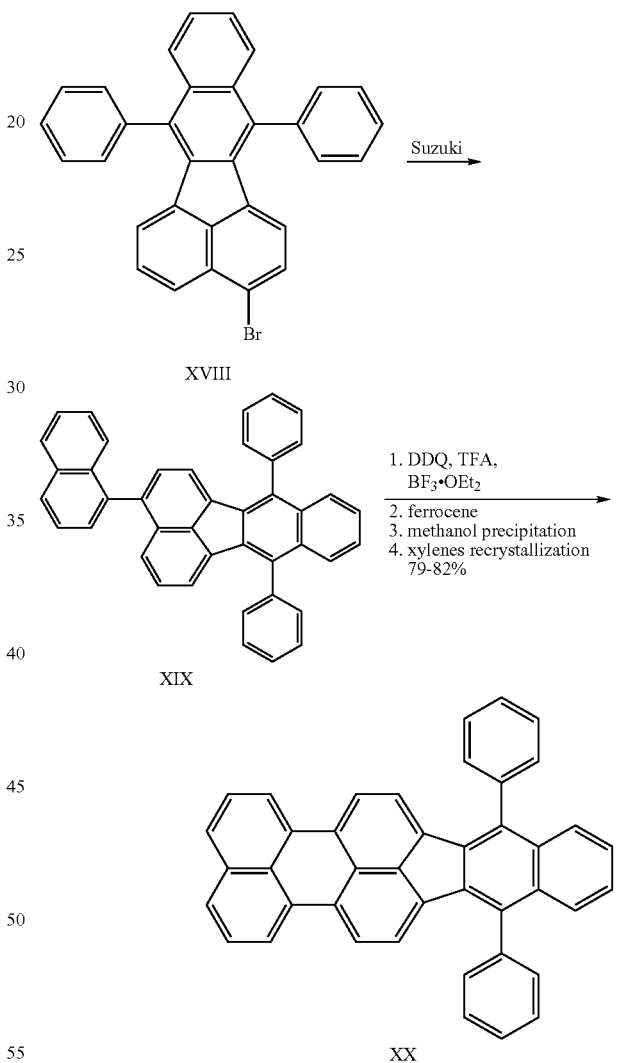

Invention, Synthesis of XX

A 1000 ml round bottom flask was charged with 5 g of XIX (3-(1-naphthyl)-7,12-diphenylbenzo[k]fluoranthene), 500 ml of trifluoroacetic acid (TFA) and 30 ml of boron trifluoride diethyletherate. A quantity of 6.42 grams of DDQ was added all at once to the stirred reaction at room temperature. This mixture was allowed to stir for 1 hour under a nitrogen atmosphere. At this time 5.29 grams of ferrocene was added in one portion, and the reaction mixture was allowed to stir for one hour. Then 2 L of methanol was added to precipitate the crude product. The crude orange XX was 89 area percent pure by LC-assay. This material was sublimed at 300° C.@700 mTorr to purity for 84% yield with a final purity of 95 area percent.

Comparative, Synthesis of XX

Anotn, U.; Göltner, C.; Müllen, K. *Chem. Ber.* 1992, 125, 2325-2330. 500 ml round bottom flask was charged with 1.58 grams of XIX and 237 ml of carbon disulfide. This reaction mixture was stirred at room temperature under a nitrogen atmosphere. To this mixture was added in one portion 1.67 g of aluminum chloride followed by 1.67 g of Cu(II)Cl2. The reaction was stirred approximately 12 hours. Water was added to quench the reaction and the organics were extracted with dichloromethane. This mixture yielded a complex LC-assay comprised of only 47 area percent of the desired product. Only after extensive high pressure reverse phase chromatography was 526 mg (33%) of XX obtained.

Conclusions for Advantages of the Inventive Method for the Synthesis of XX

The version of the inventive reaction described for the preparation of XX is advantaged over that using the Kovacic-Scholl method in both yield and purity. The inventive method yields an 89 area percent yield of product versus a 47 area percent in the comparative example. A final purification could be easily achieved in the inventive method through a sublimation of the crude product for an 84% yield whereas, the comparative method required extensive high pressure liquid chromatography to separate the product from numerous by-products and yielded a very low 33% of product based on starting material.

The two "general" inventive examples demonstrate a previously unknown method to dimerize and cyclize arenes of materials interest and yield exceptionally pure and high yield materials. Additionally, it is important to note that this method allows for avoidance of certain organic electronics materials problems. First, halogenated impurities are avoided (i.e., no free chlorides or bromides are present from reagents). Second, no metallic oxidant is used in stoichiometric quantities. Third, a six membered ring (e.g., XVII and XX) is formed from the cyclization of two arene moieties. This is not a trivial synthetic step. Modern Palladium, Nickel, Cobalt and Copper methodologies are not particularly successful at achieving such transformations. Thus, it is clear that the inventive methodology described herein for the first time fills a void in the synthetic methodology currently available.

The entire contents of the patents and other publications referred to in this specification are incorporated herein by reference.

The invention claimed is:

1. A process for forming an aryl-aryl bond comprising the step of reacting an arene hydrocarbon compound with an organic oxidant selected from the group consisting of a quinone, a quinone imine, a quinone diimine, and a nitroarene, in the presence of a Brönsted or Lewis acid, provided the reaction is conducted in the absence of free halogen impurities, and thereafter quenching the reaction with a organic or organometallic quencher.

2. The process of claim 1 in which the organic oxidant includes a substituted or unsubstituted quinone.

3. The process of claim 1 in which the organic oxidant includes a quinone selected from the group consisting of 2,3-dichloro-5,6-dicyanobenzoquinone, 1,4-benzoquinone, 1,2-benzoquinone, o-tetrafluorobenzoquinone, p-tetrafluorobenzoquinone, tetracyanobenzoquinone, o-chloranil, p-chloronil, 1,4-naphthoquinone, anthraquinone, 2,6-diphenylbenzoquinone, 2,6-di-tertbutylbenzoquinone.

4. The process of claim 1 in which the organic oxidant includes a nitroarene.

5. The process of claim 1 in which the organic oxidant includes a nitroarene selected from the group consisting of nitrobenzene, 1,2-dinitrobenzene, 1,3-dinitrobenzene and 1,4-dinitrobenzene 6. The process of claim 1 in which the organic oxidant is a nitrobenzene.

7. The process of claim 1 conducted in the presence of a Brönsted acid selected from the group consisting of trifluoromethanesulfonic acid, trifluoroacetic acid, phenylsulfonic acid, methanesulfonic acid, trichloroacetic acid, dichloroacetic acid, fluoroacetic acid, chloroacetic acid, formic acid, fluorosulfonic acid, sulfuric acid, tetrafluoroboronic acid, acetic acid, and benzoic acid.

8. The process of claim 1 conducted in the presence of a Lewis acid selected from the group consisting of $BF_3$, $BF_3.(C_2H_5)_2O$, $BCl_3$, $AlCl_3$, $Al(CH_3)_3$, $TiCl_4$, $ZrCl_4$, $SnCl_4$, $SnCl_4.5H_2O$, $SnF_4$, $VCl_4$, $SbF_5$, $ScCl_3$, $ScCl_3.6H_2O$, $Sc(CF_3SO_3)_3$, $La(CH_3CO_2).XH_2O$, $LaCl_3$, $LaCl_3.7H_2O$, $LaF_3$, $La(NO_3)_3.6H_2O$, $La(C_2O_4)_3.xH_2O$, $La(SO_4)_3.xH_2O$, $La(CF_3SO_3)_3$, $ZnCl_2$, $ZnBr_2$, $ZnF_2$, $Zn(CH_3CO_2)_2$, $Zn(CH_3CO_2)_2$, $Zn(CH_3CO_2)_2.2H_2O$, $ZnSiF_6.xH_2O$, $Zn(NO_3)_2.xH_2O$, $Zn(C_2O_4)_2.xH_2O$, and $Nd(CF_3SO_3)_3$.

9. The process of claim 1 conducted in presence of both a Lewis acid and a Brönsted acid.

10. The process of claim 1 in which the reaction is terminated by a quenching agent which is a compound capable of a reductive electron transfer process.

11. The process of claim 1 in which the reaction is terminated by a quenching agent selected from the group consisting of silver, magnesium, zinc, manganese, iron, cobalt, sodium, potassium, aluminum, ferrocene, zirconocene, lithium, tin, methanol, ethanol, triethylamine, triphenylamine, trimethoxybenzene.

12. The process of claim 1 in which the reaction is terminated by a quenching agent which is a metal-organic complex capable of a reductive electron transfer process.

13. The process of claim 12 in which the quenching agent is ferrocene.

14. The process of claim 1 conducted at a temperature between
−20° C. and 85° C.

15. The process of claim 1 in which the reaction temperature is less than 25° C.

16. A process for forming an aryl-aryl bond comprising the step of reacting two arene hydrocarbon molecules with an organic oxidant, selected from the group consisting of a quinone, a quinone imine, a quinone diimine, and a nitroarene, in the presence of a Brönsted or Lewis acid, provided the reaction is conducted in the absence of free halogen impurities, and thereafter quenching the reaction with an organic or organometallic quencher, to form an intermolecular bond between the two molecules.

17. The process of claim 16 in which the organic oxidant is a substituted or unsubstituted quinone.

18. The process of claim 16 in which the arene hydrocarbon compound is a polycyclic aromatic hydrocarbon.

19. The process of claim 16 in which the arene hydrocarbon is selected to form a bis-fluoranthene compound.

20. The process of claim 16 in which the arene hydrocarbon is selected to form a diindeno[1,2,3-cd:1',2',3'-lm]perylene capable of fluorescent emission in the green to red region of the visible absorption spectrum.

21. The process of claim 16 in which the arene hydrocarbon is selected to form an indenoperylene[1,2,3-cd]perylene compound.

22. The process of claim 16 in which the arene hydrocarbon is selected to form a perylene compound.

23. The process of claim 16 in which the arene hydrocarbon is selected to form a bis-anthracene compound.

24. The process of claim 16 in which the arene hydrocarbon is selected to form a bis-pyrene compound.

25. The process of claim 16 in which the reaction is terminated by contact with a quenching agent.

26. A process for forming an aryl-aryl bond comprising the step of reacting a single arene hydrocarbon molecule with an organic oxidant selected from the group consisting of a quinone, a quinone imine, a quinone diimine, and a nitroarene, in the presence of a Brönsted or Lewis acid provided the reaction is conducted in the absence of free halogen impurities, and thereafter quenching the reaction with an organic or organometallic quencher, to form an intramolecular bond effecting the formation of a carbocyclic ring.

27. The process of claim 26 in which the arene hydrocarbon is selected to form intramolecularly a five-membered carbocyclic ring or to form intramolecularly a six-membered carbocyclic ring.

28. The process of claim 26 in which the organic oxidant is a substituted or unsubstituted quinone.

29. The process of claim 26 in which the reaction is terminated by a quenching agent.

30. The process of claim 1 in which the arene hydrocarbon is 7,12-diphenylbenzo[k]fluoranthene (XV), the organic oxidant is 2,3-dichloro-5,6-dicyanobenzoquinone, the Brönsted acid is trifluoroacetic acid, the Lewis acid is boron trifluoride diethyletherate, and the quenching agent is ferrocene and the product is dibenzo {[f,f']-4,4',7,7'-tetraphenyl}-diindeno[1,2,3-cd:1',2',3'-lm]perylene.

31. The process of claim 1 in which the arene hydrocarbon is (3-(1-naphthyl)-7,12-diphenylbenzo[k]fluoranthene), XIX, the organic oxidant is 2,3-dichloro-5,6-dicyanobenzoquinone, the Brönsted acid is trifluoroacetic acid, the Lewis acid is boron trifluoride diethyletherate, and the quenching agent is ferrocene and the product is benzo{[f]-4,7-diphenyl}-indeno[1,2,3-cd]perylene.

32. The process of claim 1 in which the arene hydrocarbon is represented by formula XVI,

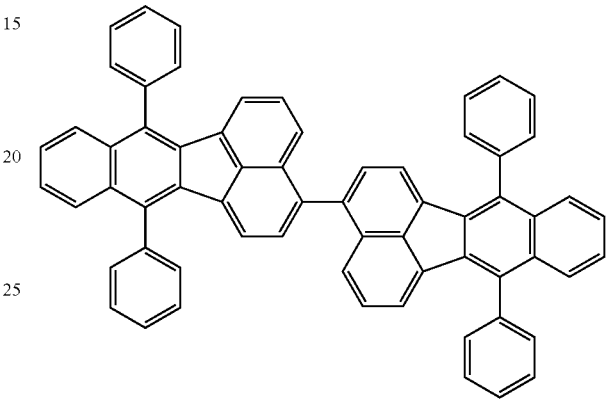

XVI wherein the organic oxidant is nitrobenzene, the Brönsted acid is trifluoromethanesulfonic acid, and the quenching agent is triethylamine.

* * * * *

UNITED STATES PATENT AND TRADEMARK OFFICE
CERTIFICATE OF CORRECTION

PATENT NO. : 7,368,624 B2
APPLICATION NO. : 10/812692
DATED : May 6, 2009
INVENTOR(S) : Christopher T. Brown et al.

It is certified that error appears in the above-identified patent and that said Letters Patent is hereby corrected as shown below:

| | |
|---|---|
| Title Page, Col. 2, Item [56] Line 21 (Other Publications) | Delete "Synhetic" and insert -- Synthetic --, therefor. |
| Title Page, Col. 2, Item [74] Line 1 | Delete "Kluegal" and insert -- Kluegel --, therefor. |
| Column 30, Line 8 | In Claim 5, after "1,4-dinitrobenzene" insert -- . --. |
| Column 30, Line 22 | In Claim 8, delete "La(CH3CO2).XH2O," and insert -- La(CH3CO2).xH2O, --, therefor. |
| Column 31, Line 16 | In Claim 26, delete "acid" and insert -- acid, --, therefor. |

Signed and Sealed this

Nineteenth Day of January, 2010

David J. Kappos
*Director of the United States Patent and Trademark Office*